United States Patent [19]

Matsuo et al.

[11] 4,268,527

[45] May 19, 1981

[54] METHOD FOR PRODUCING CACAO BUTTER SUBSTITUTE

[75] Inventors: Takaharu Matsuo: Norio Sawamura, both of Osaka; Yukio Hashimoto, Kishiwada; Wataru Hashida, Osaka, all of Japan

[73] Assignee: Fuji Oil Company, Ltd., Japan

[21] Appl. No.: 92,096

[22] Filed: Nov. 7, 1979

[30] Foreign Application Priority Data

Nov. 21, 1978 [JP] Japan ............................... 53-144736

[51] Int. Cl.[3] .......................... A23D 5/02; C12P 7/64

[52] U.S. Cl. ...................................... 426/33; 426/607; 435/134

[58] Field of Search .......................... 426/33, 35, 607; 435/134, 271

[56] References Cited

U.S. PATENT DOCUMENTS

| | | | |
|---|---|---|---|
| 2,485,779 | 10/1949 | Sanders | 435/271 |
| 2,769,750 | 11/1956 | Harris | 435/248 |
| 2,924,555 | 2/1960 | Reese | 435/74 |
| 3,012,890 | 12/1961 | Dutton et al. | 426/607 X |
| 3,190,753 | 6/1965 | Claus et al. | 435/134 X |
| 3,492,130 | 1/1970 | Harwood | 426/607 |
| 3,878,231 | 4/1975 | Harwood | 426/607 X |
| 4,032,405 | 6/1977 | Tatsumi et al. | 435/134 X |

FOREIGN PATENT DOCUMENTS

| | | | |
|---|---|---|---|
| 49-22696 | 6/1974 | Japan | 426/33 |
| 50-25544 | 8/1975 | Japan | 426/33 |
| 52-104506 | 9/1977 | Japan | |

OTHER PUBLICATIONS

Sreenivasan, B. "Interesterification of Fats", J. Am. Oil Chem. Soc., 55, 1978, pp. 796–804.

Kartha, A. R. S., "The Glyceride Structure of Natural Fats III" J. Am. Oil Chem. Soc., 31, 1954, pp. 85–88.

Alford, J. A. et al., "Jour. Lipid Res." 5, (1964), pp. 390–394.

*Primary Examiner*—Robert A. Yoncoskie

*Attorney, Agent, or Firm*—Wenderoth, Lind & Ponack

[57] ABSTRACT

There is provided a method for producing a cacao butter substitute by transesterification of fats and oils containing glycerides rich in the oleyl moiety at the 2-position with an alcohol ester of stearic acid and/or palmitic acid in the presence of a lipase having reaction specificity to the 1,3-position of triglycerides and not more than 0.18% by weight of water based on the total weight of the reaction mixture. By this method, a cacao butter substitute, rich in 1,3-distearyl-2-oleyl compound and 1-palmityl-2-oleyl-3-stearyl compound is obtained, in a high reaction yield with few by-products.

7 Claims, No Drawings

METHOD FOR PRODUCING CACAO BUTTER SUBSTITUTE

The present invention relates to a method for producing a cacao butter substitute which can be substituted for a cacao butter in chocolate production and the like. More particularly, it relates to an improved method for producing a cacao butter substitute in a high reaction yield with few by-products by transesterification of fats and oils comprising glycerides rich in oleyl moiety at the 2-position and one or more fatty acids, by using a lipase having reaction specificity to the 1,3-position of triglycerides.

As a method for improving properties of fats and oils, it has been proposed to subject the fats and oils to transesterification with other fats and oils or fatty acids by using a catalyst such as an alkali metal, an alkali metal alkoxylate, an alkali metal hydroxide and the like. It has also been proposed to carry out the transesterification by using a lipase instead of using the above catalyst even in the presence of water. When a lipase is used, fats and oils containing triglycerides having the desired configuration and characteristics can conveniently be produced by the transesterification, since reaction specificity of a lipase can be utilized in order to regulate fatty acid residues bonded to a certain position of triglycerides. That is, a selective transesterification reaction can readily be carried out.

The above transesterification occurs as a result of a reversible reaction which involves both a hydrolysis of triglycerides to di- and monoglycerides or to glycerin and fatty acids and a synthesis of the hydrolyzates formed to triglycerides and the like. When an excess amount of water is present in the reaction system, equilibrium of the reversible reaction is moved to the side wherein the hydrolysis predominates, which causes formation of a large amount of hydrolyzates and lowers the yield of the triglycerides. Among the hydrolyzates, the free fatty acids can relatively easily be removed from the reacted product by the conventional refining technique, but the diglycerides etc. are hardly removed. Such unremovable hydrolyzates cause decrease in the quality of cacao butter-like triglycerides. However, it has been thought that it is necessary to carry out the transesterification in the presence of a certain amount of water to increase the transesterification rate, because the transesterification occurs as a result of hydrolysis.

Besides, in the production of a cacao butter substitute, it is desirable to obtain fats and oils of glycerides which comprise predominantly 1,3-distearyl-2-oleyl compound and 1-palmityl-2-oleyl-3-stearyl compound (hereinafter, referred to as "1,3-distearyl-2-oleyl compound etc."). Then, for example, a selective transesterification reaction of fats and oils having a high content of oleic acid residue at 2-position with stearic acid has been employed to obtain the desired fats and oils of glycerides. However, when a lipase is used as a catalyst in this transesterification, only a portion of stearic acid added to fats and oils can directly take part in the reaction, since stearic acid, which has a high melting point of about 70° C., is usually solid at a temperature which the lipase can maintain its activity. Even if a large amount of stearic acid is added to the reaction system in order to increase the amount of stearic acid residue in the product, most of the stearic acid added does not take part in the reaction since it does not dissolve in the fats and oils and is still kept in a stable solid state and is separated out from the reaction system. Although stearic acid in a solid state can dissolve in the reaction system as the transesterification progresses, the amount of dissolution of the solid stearic acid is small since the dissolution of the solid stearic acid is restricted by dissolution of other fatty acids derived from the glycerides by transesterification thereof with stearic acid. Moreover, not only stearic acid but also the other fatty acids take part in the synthesis reaction in the transesterification since the ratio of the other fatty acids to stearic acid in solution becomes large gradually. Therefore, it is difficult to obtain a transesterified fats and oils product containing a lot of stearic acid residue. When palmitic acid is used alone or together with stearic acid instead of stearic acid in the above transesterification, similar results are obtained.

Thus, generally, the transesterification with a lipase is carried out by using an inert organic solvent which does not affect the lipase to be used, such as n-hexane and the like, so that fats and oils and a fatty acid to be used are kept in solution. However, this transesterification using an organic solvent requires very expensive closed-system reaction facilities since, as an organic solvent, a volatile solvent is primarily used. Moreover, the solvent used should be separated and recovered from the reaction product, which results in a high cost of the product.

An object of the present invention is to provide an improved method for producing a cacao butter substitute, the primary components of which are "1,3-distearyl-2-oleyl compound etc."

Another object of the present invention is to provide an improved method for producing a cacao butter substitute in a high reaction yield and with few by-products by a transesterification reaction using a lipase without any organic solvent.

These objects as well as other objects and advantages of the present invention will become apparent to those skilled in the art from the following description.

According to the present invention, the desired cacao butter substitute containing as primary components "1,3-distearyl-2-oleyl compound etc." can be produced in a high reaction yield with few by-products, such as diglycerides and free fatty acids, by transesterification of fats and oils comprising glycerides rich in the oleyl moiety at the 2-position and a lower alcohol ester of stearic acid and/or palmitic acid, in the presence of a lipase having reaction specificity to 1,3-position of triglycerides in the presence of not more than 0.18% by weight of water based on the total weight of the reaction mixture.

The term "reaction yield" used herein means the increase in the content of "1,3-distearyl-2-oleyl compound etc." in the resulting fats and oils comprising glycerides after completion of the reaction compared to that before the reaction. In the working examples described hereinafter, however, the content of "1,3-distearyl-2-oleyl compound etc." in glycerides after completion of the reaction is disclosed.

As described above, stearic acid and/or palmitic acid, used in a conventional reaction, have a high melting point and, in many cases, it is necessary to use an organic solvent. To the contrary, in the present invention, since a lower alcohol ester of stearic acid and/or palmitic acid is used instead of stearic acid and/or palmitic acid per se and it has a low melting point and readily dissolves in fats and oils to be used, no organic solvent is substantially required. Therefore, recovery of any solvent after completion of the reaction is not required in the present invention. Moreover, in comparison with stearic acid or palmitic acid used in a conventional reaction, a lower alcohol ester of these acids has a high reactivity in the transesterification and thereby an extremely superior reaction yield is attained. Additionally, lower alcohol esters of stearic acid and/or palmitic acid remained in the reaction mixture after completion of the reaction as well as lower alcohol esters formed with other fatty acids derived from fats and oils used. As the result of transesterification thereof have both a lower melting point and a lower boiling point than those of stearic acid and/or palmitic acid as well as those of other free fatty acids presented in a conventional reaction. Therefore, in the present invention, fatty acids remaining in the reaction mixture can readily be separated and recovered by a conventional method such as steam distillation.

In the transesterification of the present invention, excessive hydrolysis of triglycerides can mostly be inhibited by carrying out the transesterification reaction in the presence of not more than 0.18% by weight of water based on the total weight of the reaction mixture, in addition to the use of lower alcohol ester(s) of stearic acid and/or palmitic acid which are superior in various properties to stearic acid and/or palmitic acid per se used in a conventional reaction.

As described above, the transesterification is a sort of reversible reaction involving a hydrolysis reaction and a synthesis reaction. Thus, when water is present in the reaction system, it is consumed in the hydrolysis reaction and the equilibrium of the reversible reaction is shifted in such a direction that the amount of hydrolyzates such as diglycerides, free fatty acids and the like increases. Therefore, in order to control formation of by-products, it is necessary to decrease the water content in the reaction mixture. However, on the other hand, the presence of a certain amount of water is necessitated so as to activate the lipase to be used. Accordingly, in conventional transesterification reactions, water is usually added to the reaction system notwithstanding the undesirable formation of by-products.

To the contrary, according to the method of the present invention, since lower alcohol esters of stearic acid and/or palmitic acid having a high reactivity are employed, it is possible to extremely lower the water content in the reaction system in comparison with that in a conventional transesterification reaction using a lipase. Thus, in the present invention, it is possible to carry out the transesterification in a high reaction yield in the presence of a very small amount of water such as not more than 0.18% by weight based on the total weight of the reaction mixture, and hence, there is no problem of increasing by-products formation.

When the water content in the reaction mixture is more than 0.18% by weight, the amount of by-products becomes excessive and it is difficult to remove a large amount of diglycerides. When the water content is not more than 0.18% by weight, the reaction product can readily be refined by mere removal of the remaining free fatty acids and lower alcohol esters of fatty acids therefrom. In view of its use as a raw material for a cacao butter substitute, it is preferable that the amount of remaining diglycerides in the reaction product be not more than about 12% by weight based on the weight of the reaction product. When the fats and oils contain lesser amount of water, it is more difficult to dehydrate them. The starting fats and oils which are obtained by dehydration using an alkali metal catalyst have usually a water content of about 0.01% by weight, and even when these fats and oils are used, lipase can be used. The water content in the reaction mixture is also included that originated from the enzyme. Thus, the lower limit of water content in the reaction mixture is not critical, but it is preferable that the water content in a reaction mixture be in the range of 0.01 to 0.18% by weight based on the total weight of the reaction mixture.

Examples of fats and oils of glycerides containing oleic acid residue at 2-position used in the present invention are palm oil, olive oil, shea butter, illipe butter, Borneo tallow, sal fat (Shorea Robusta), a fractionated fat thereof and the like. These fats and oils can be used alone or in combination thereof. The lower alcohol ester of stearic acid and/or palmitic acid includes an ester of the acids with an aliphatic alcohol having 1 to 5 carbon atoms. Preferred examples of a lower alcohol ester of stearic acid are methyl stearate, ethyl stearate, propyl stearate and butyl stearate. Preferred examples of a lower alcohol ester of palmitic acid are methyl palmitate, ethyl palmitate, propyl palmitate and butyl palmitate. These esters can be used alone or in combination thereof.

For producing a cacao butter substitute according to the method of the present invention, generally, the lower alcohol ester of stearic acid and/or palmitic acid is admixed with the above fats and oils of glycerides in an amount of 0.2 to 5 times of the weight of the fats and oils. When using both lower alcohol esters of stearic acid and palmitic acid, the mixing ratio of a lower alcohol ester of stearic acid to that of palmitic acid is determined according to the particular composition of fatty acid residues at 1,3-position of fats and oils to be used. For example, when a palm oil fraction wherein stearic acid residue at 1,3-position of the glyceride is contained in an amount of less than that of palmitic acid residue is used, a lower alcohol ester of stearic acid is predominantly added thereto. To the contrary, when a shea butter fraction wherein stearic acid residue at 1,3-position of the glyceride is greater than palmitic acid residue is used, a lower alcohol ester of palmitic acid is predominantly added thereto. And when olive oil wherein both stearic residue and palmitic residue at 1,3-position is contained in an amount of less than that of oleic residue is used, both lower alcohol esters of stearic acid and palmitic acid are added thereto. When the lower alcohol ester of stearic acid and/or palmitic acid is admixed with fats and oils in an amount of less than 0.2 times of the weight of the fats and oils, the content of 1,3-distearyl-2-oleyl compound etc. in the reaction product may be insufficient for a cacao butter substitute. While the content of 1,3-distearyl-2-oleyl compound etc. in the reaction product is sufficient for a cacao butter substitute when the lower alcohol ester of stearic acid and/or palmitic acid is added in an amount of 0.2 to 5 times of the weight of fats and oils to be used, a larger amount of the lower alcohol ester of stearic acid and/or palmitic acid may be added in order to shorten reaction time.

A lipase used in the present invention may be any known lipase having reaction specificity to 1,3-position of triglycerides. Preferred examples of the lipase are those produced by microorganisms such as Rhizopus, Aspergillus and Mucor and a pancreatic lipase, rice bran lipase and the like. Particularly, those lipases of *Rhizopus niveus, Rhizopus japonicus, Mucor javanicus* and *Aspergillus niger* are preferable. Although the lipase may directly be added to the reaction mixture as it is, it is usually used in the form that it is adsorbed onto a known carrier such as diatomaceous earth, alumina, charcoal and the like. It is preferable to use the lipase in the form absorbed onto a carrier, since water in the reaction mixture is also adsorbed onto the carrier, whereby it contributes primarily to activate the lipase and formation of by-products is controlled. When a commercially available lipase is used, the lipase is usually added to the reaction mixture in an amount of 0.1 to 10% by weight based on the total weight of the reaction mixture.

The transesterification of the present invention is carried out at 20° to 60° C., at e.g. which the lipase is active and relatively stable. Reaction time is not critical but, is usually in the range of 10 to 240 hours. The reaction of the present invention can be performed not only by a batch system but also by continuous system.

As described hereinbefore, according to the method of the present invention, fats and oils containing large amount of "1,3-distearyl-2-oleyl compound etc." useful for a cacao butter substitute can be produced in a high reaction yield with few by-products, by transesterification, which can hardly be obtained by the conventional method using stearic acid and/or palmitic acid per se. Moreover, in the present invention, the lower alcohol ester of stearic acid and/or palmitic acid does not necessarily require use of an organic solvent and it can readily be separated and removed from the reaction mixture after the reaction.

The following examples further illustrate the present invention in detail but are not to be construed to limit the scope thereof. In the examples, all "%" are by weight unless otherwise stated.

EXAMPLE 1

A fractionated palm oil containing triglycerides having the 2-oleyl moiety (84.4% based on the total triglycerides) and diglycerides (4.1%), the amount of "1,3-distearyl-2-oleyl compound etc." thereof being 15.4%, was heat-dried under vacuum.

Likewise, a commercially available methyl stearate (containing 89% of methyl stearate and about 11% of methyl palmitate) was dried.

Methyl stearate (500 g) was admixed with the above dried oil (500 g). The water content of the resulting mixture was 0.02%. To the mixture was added and dispersed a powdered celite-enzyme preparation (50 g) (which was prepared by adsorbing 17 g of a lipase of *Rhizopus niveus* onto the diatomaceous earth carrier (celite) and contained 2% of water) and the mixture was reacted at 40° C. for 72 hours with stirring at 200 r.p.m. After the completion of the reaction, the celite-enzyme preparation adsorbing the lipase was filtered off. Steam was blown into the resulting reaction mixture and the remaining free fatty acids and methyl esters of fatty acids were distilled off at 170° C. under a pressure of 1 mmHg to obtain the desired reaction product (475 g).

The reaction product thus obtained contained 93.7% of triglycerides and 6.3% of diglycerides. The triglycerides were composed of 8.4% of tri-saturated fatty acids-glycerides, 76.8% of di-saturated fatty acids-mono-unsaturated fatty acid-glycerides and 14.8% of other triglycerides. The di-saturated fatty acids-mono-unsaturated fatty acid-glycerides were composed of 20.9% of 1,3-dipalmityl-2-oleyl compound, 48.8% of 1-palmityl-2-oleyl-3-stearyl compound, 29.2% of 1,3-distearyl-2-oleyl compound and 1.1% of the other glyceride compounds.

Therefore, the content of "1,3-distearyl-2-oleyl compound etc." (reaction yield) of the reaction product was 56.1% and this product was quite similar to natural cacao butter which contains about 60% of "1,3-distearyl-2-oleyl compound etc."

EXAMPLE 2

The reaction product of Example 1 (400 g) was fractionated with n-hexane to obtain a high melting point fraction (53 g) and a low melting point fraction (347 g). The low melting point fraction was refined by bleaching and deodorization according to a standard method. The components of the refined fraction were analyzed.

The results are shown in Table 1. In comparison, the components of natural cacao butter are also shown in Table 1.

TABLE 1

| | Fats and oils | |
|---|---|---|
| Components | Example 1 (%) | Cacao butter (%) |
| Total triglycerides | 95.0 | 96.2 |
| Total diglycerides | 5.0 | 3.8 |
| Triglycerides components[a] | | |
| Tri-S-glycerides | 1.5 | 1.0 |
| Di-S-mono-U-glycerides | 83.2 | 82.0 |
| Mono-S-di-S-glycerides | 13.0 | 15.2 |
| Tri-U-glycerides | 2.3 | 1.8 |
| Di-S-mono-U-glycerides components | | |
| 2-Unsaturated fatty acid | 98.1 | 100 |
| 2-Saturated fatty acid | 1.9 | 0 |
| 1,3-S-2-U-glycerides components[b] | | |
| St O St | 30.1 | 34.3 |
| St O P | 49.3 | 49.0 |
| P O P | 19.8 | 16.2 |
| Others | 1.3 | 0.4 |

[Remarks]:
[a]S: saturated fatty acid; U: unsaturated fatty acid
[b]St: stearic acid; O: oleic acid; P: palmitic acid As is clear from Table 1, the resulting fats and oils of Example 1 had a quite similar triglycerides composition to that of natural cacao butter.

When a milk chocolate was produced by using the fats and oils obtained above according to a standard method, heat resistance, melting properties in the mouth, snapping properties and anti-blooming properties of the resulting chocolate were similar to those of a chocolate produced by using natural cacao butter.

EXAMPLE 3

A low melting point fraction of a fractionated sal fat (200 g) (containing 5.3% of diglycerides, the content of "1,3-distearyl-2-oleyl compound etc." being 14.6%), methyl stearate (100 g) and methyl palmitate (100 g) were each dried under vacuum and were mixed. The water content of the mixture was 0.02%. To the mixture was added and dispersed a celite-enzyme preparation (20 g) (adsorbing 2 g of a lipase of *Mucor javanicus* and containing 3% of water) and the mixture was reacted at 45° C. for 72 hours with stirring at 200 r.p.m. After removal of the celite-enzyme preparation by filtration under reduced pressure, steam was blown into the resulting mixture and free fatty acids and methyl esters of fatty acids were distilled off at 170° C. under a pressure of 1 mmHg to obtain the desired reaction product (196 g).

The reaction product contained 92.2% of triglycerides and about 7.8% of diglycerides. The content of "1,3-distearyl-2-oleyl compound etc." in the triglycerides was 43.7% based on the reaction product.

When the reaction product obtained above is subjected to fractionation in the same manner as described in Example 2, the reaction product becomes satisfactory for use as a cacao butter substitute.

EXAMPLE 4

Three portions (each 200 g) of a medium melting point fraction of palm oil and 120 g, 200 g and 400 g of ethyl stearate (containing 11% of ethyl palmitate) were each dried under vacuum and they were mixed respectively. The water content of each mixture was 0.02%. In the same manner as in Example 3, to the mixture containing 120 g of ethyl stearate was added the same celite-enzyme preparation as used Example 3. Likewise, 20 g and 30 g of the preparation were each added to the mixtures containing 200 g and 400 g of ethyl stearate, respectively. Each mixture was reacted at 45° C. with stirring at 200 r.p.m. The resulting mixtures were subjected to steam distillation and the triglycerides compositions thereof were analyzed. The results are shown in Table 2.

TABLE 2

| Materials | Triglycerides composition (%)[a] | |
|---|---|---|
| | St O ST + P O St | P O P |
| Medium m.p. fraction of palm oil | 16.2 | 67.3 |
| Ethyl stearate 120 g | 53.5 | 24.3 |
| Ethyl stearate 200 g | 60.9 | 18.3 |
| Ethyl stearate 400 g | 68.3 | 12.9 |

[Remarks]:
[a]: St, O and P are as defined in Table 1.

As is clear from Table 2, each reaction product has a triglycerides composition suitable for a cacao butter substitute.

REFERENCE EXAMPLE

A medium melting point fraction of palm oil (diglycerides 5.0%, "1,3-distearyl-2-oleyl compound etc." 15.4%) and an equal amount of methyl stearate (containing 11% of methyl palmitate) were each dried under vacuum and mixed together. The water content of the mixture was 0.02%.

A Lipase of *Mucor javanicus* (20 g) was adsorbed onto celite (diatomaceous earth) to obtain a celite-enzyme preparation (200 g) (containing 1.6% of water).

To two portions (each 400 g) of the above mixture were added 0.4 g and 0.6 g of water, respectively. After water was homogeneously dispersed into the mixtures, 20 g of the above celite-enzyme preparation were each added to the mixtures and the mixtures were each reacted at 45° C. for 72 hours with stirring at 200 r.p.m. In the same manner as in Example 3, the mixtures were subjected to steam distillation and triglycerides compositions thereof were analyzed. The results are shown in Table 3. In comparison, the results obtained by the same procedure except that no water was added are also shown in Table 3.

TABLE 3

| Water added | Diglycerides (%) | P O St + St O St[a] (%) | Water in the reaction system (%) |
|---|---|---|---|
| 0.4 g | 12.9 | 54.5 | 0.20 |
| 0.6 g | 15.0 | 54.0 | 0.25 |
| None | 8.8 | 56.1 | 0.10 |

[Remarks]:
[a]P, O and St are as defined in Table 1.

As is clear from Table 3, when the water content in the reaction system increases, the amount of diglycerides also increases, which is undesirable for a cacao butter substitute.

EXAMPLE 5

In the same manner as described in Example 1, a mixture substrate (water content: 0.02%) was prepared from palm oil and methyl stearate. Into the mixture substrate (100 g) was added and dispersed an enzyme of *Rhizopus japonicus* cells (8 g, water content: 2.0%), and the mixture was stirred at 40° C. at 200 r.p.m. for 5 days. The reaction product was treated in the same manner as described in Example 1 and the composition of the product was analyzed likewise.

The recovered enzyme was repeatedly used after dispersing into a fresh mixture substrate and was repeatedly reacted, and the resulting products were analyzed likewise. The results are shown in Table 4.

TABLE 4

| | Repeating times | | | |
|---|---|---|---|---|
| | Once | Twice | Three times | Four times |
| Reaction times (days) | 5 | 5 | 6 | 8 |
| Content of diglycerides (%) | 6.2 | 5.5 | 5.8 | 5.5 |

As is clear from the above result, reaction times (days) should be longer with increase of the repeating times, and the products obtained by using the enzyme repeatedly had a lower content of diglycerides in comparison with that of the product obtained first time. However, with respect to other components of the products, similar results were obtained, which means that the enzyme can be used repeatedly.

The present invention being thus described, it will be obvious that the same way be varied in many ways. Such modifications are not to be regarded as a departure from the spirit and scope of the present invention, and all such modifications are intended to be included within the scope of the following claims.

What is claimed is:

1. In a method for producing a cacao butter substitute by transesterifying fats and oils comprising glycerides containing the oleyl moiety at the 2-position with one or more fatty acids, by using a lipase having reaction specificity to 1,3-position of triglycerides, the improvement which comprises transesterifying said fats and oils with an aliphatic alcohol ester of stearic acid, palmitic acid or mixtures thereof in the presence of not more than 0.18% by weight of water based on the total weight of the reaction mixture.

2. A method according to claim 1, wherein said fats and oils are a member selected from the group consisting of palm oil, olive oil, shea butter, illipe butter, Borneo tallow, sal fat and a fractionated fat thereof, and a mixture thereof.

3. A method according to claim 1, wherein said lipase is added in an amount of 0.1 to 10% by weight based on the total weight of the reaction mixture.

4. A method according to claim 1, wherein said alcohol ester of stearic acid is a member selected from the group consisting of methyl stearate, ethyl stearate, propyl stearate and butyl stearate.

5. A method according to claim 1, wherein said alcohol ester of palmitic acid is a member selected from the group consisting of methyl palmitate, ethyl palmitate, propyl palmitate and butyl palmitate.

6. A method according to claim 1, wherein said alcohol ester of stearic acid, palmitic acid or mixtures thereof is admixed with said fats and oils in an amount of 0.2 to 5 times the weight of said fats and oils.

7. A method according to claim 1, wherein the water content of the reaction mixture is 0.01 to 0.18% by weight.

* * * * *